United States Patent [19]
Elliott

[11] 3,980,083
[45] Sept. 14, 1976

[54] MEDICAMENT INFUSOR UNIT
[75] Inventor: Phillip M. Elliott, Schiller Park, Ill.
[73] Assignee: Illinois Tool Works Inc., Chicago, Ill.
[22] Filed: Feb. 13, 1975
[21] Appl. No.: 549,563

[52] U.S. Cl............................ 128/220; 128/218 D; 128/218 DA
[51] Int. Cl.² ........................................ A61M 5/00
[58] Field of Search................ 128/220, 221, 218 N, 128/218 D, 218 DA, 215, 272, 216

[56] References Cited
UNITED STATES PATENTS

| | | | |
|---|---|---|---|
| 2,448,898 | 9/1948 | Lockhart | 128/220 |
| 2,693,183 | 11/1954 | Lockhart | 128/216 |
| 2,771,879 | 11/1956 | Salisbury, Jr. | 128/216 |
| 2,959,170 | 11/1960 | Laub | 128/218 N |
| 3,098,482 | 7/1963 | O'Sullivan | 128/220 |
| 3,128,766 | 4/1964 | Mizzy | 128/220 |
| 3,376,866 | 4/1968 | Ogle | 128/220 |
| 3,552,387 | 1/1971 | Stevens | 128/218 M |
| 3,724,460 | 4/1973 | Gomez et al. | 128/218 M |
| 3,838,689 | 10/1974 | Cohen | 128/218 M |
| 3,890,972 | 6/1975 | Standley et al. | 128/220 |

Primary Examiner—John D. Yasko
Attorney, Agent, or Firm—J. R. Holvorsen; R. W. Beart

[57] ABSTRACT

An infusor unit for dispensing a medicament by injection including a vial having an open end and a closed end and a resilient piston adapted to be initially partially inserted into said vial. The piston having a central through bore which is sealed by a transverse diaphragm and a chamber formed at one end of the piston by the diaphragm and a reduced entryway at its open end to define internal shoulder means. A substantially rigid hollow tubular infusor means which includes means for securing a sharpened cannula which extends outwardly from one end and in communication with the transparent interior of said infusor. The opposite end of the infusor having hollow means for sealing engagement with the piston bore for pre-assembly and, subsequently, to cooperatively penetrate said diaphragm to provide access of the hollow infusor and its connected passageway with the cannula to the interior of the piston sealed vial.

46 Claims, 20 Drawing Figures

MEDICAMENT INFUSOR UNIT

BACKGROUND OF THE INVENTION

In present day medical sciences, there is a distinct trend toward the unit-dose systems wherein a predetermined quantity of drugs can be pre-packaged and stored for extended periods of time and usable on quick notice for emergency situations which may arise in the clinic or the operating room. Heretofore, conventional syringes have been utilized to aspirate the medicament from a closed vial by puncturing a diaphragm across the vial with the cannula, aspirating the syringe, and thereby filling the syringe for usage. This procedure is quite time consuming and, additionally, has the disadvantage of drugs being aspirated from a vial and the drug replaced by water or a similar liquid substance.

Several unit-dose devices have been available on the market but have had several distinct disadvantages. One such device requires an expensive holder to which a sterilized cannula must be attached and, due to the expense of the holder, is often not readily available at the time of need, the expense precluding the availability of additional holders. Additionally, such devices do not have means for pre-assembly in a non-activated condition and their more common activation movement requires at least a turn of some rotational degree and, more commonly, a combination of insertion, seal break-off, and a twisting motion which is relatively complex to the uninitiated user. Additionally, none of the existing devices provides aseptic protection over all drug container and drug contact surfaces to the moment of infusion. At best, such devices provide minimal drug contact surfaces which, up to the moment of aspiration for a show of blood when a venipuncture is necessary, are not exposed to the drug, but which immediately upon aspiration pull their plunger or plug back across vial surfaces which have been exposed to the air and which consequently can subject the infused drugs to aerobic contamination.

Probably one of the most important deficiencies of such existing prior art is that none of these devices provides a visual observation of aspirated blood without introducing the blood to the drug container.

Lastly, because of the typically rotational activation nature of such existing syringe devices, these devices are necessarily round tubular members or generally cylindrical in shape, thereby requiring cylindrical embodiments in co-acting holder, activators and similarly related components of such devices.

Prior art devices having the limitations enumerated above can be found in the United States Pats. issued to R. W. Ogle, such as Nos. 3,303,846; 3,330,280; 3,376,866; 3,378,008; and the patent to Fred M. Killinger, no. 3,841,329.

SUMMARY OF THE INVENTION

It is an object of this invention to provide a simple, convenient to use, parenteral drug containing device that can be stored for long periods of time and, at the moment of need, easily and quickly readied for use with a single linear movement.

Another object of this invention is to provide a device which is capable of giving a readily observable indication that a venipuncture has been made by a show of aspirated blood within the device that does not necessitate drawing the blood back into the drug containing vial.

Further, in the interest of maintaining good prevention of contamination, it is an object of this invention to preclude contact from the surrounding air of any drug container surface which will be at any time in contact with the drug.

An additional object to the invention is to provide an infusor unit which, once a venipuncture or needle entry is made, permits the injection of several vials of the same or varying drug content by having the ability to disengage the vial without or with minimum aspiration of blood or body fluid into the removed vial.

Aspirating in a unit-dose system should occur only at desired times. This is accomplished in the present invention by keeping the retentive force of the piston or plug to the vial wall at a control level. By controlling the drag on the vial wall and retention of the infusor unit probe to the plug, a low level of aspirating pull can be exerted against the plug without disengagement. An abruptly higher pull disengages the probe from the plug leaving it in the vial without aspiration. The plug, with the probe removed, reseals the vial or simply remains at the bottom of the empty vial ready for discard. Meanwhile, the infusor unit, with the cannula still implanted in the venipuncture, is ready to receive and engage a fresh vial. In this way, several drugs or vial quantities can be injected with a single venipuncture. A secondary advantage of the disengagement of the probe from the plug or piston is its non-reuse. If the plug were designed to aspirate easily it would encourage use of aspirating drugs from a bulk container. Making aspiration difficult encourages single use and disposal with its inherent sterile advantages. Since the device is intended and designed for single usage the disengagement of the plug from the probe defeats mis-use, re-use, making the package more security conscious and substantially tamper-proof.

All of the afore-mentioned objectives can be shown in the detailed description which follows. These objectives, together with the simple, economical manufacture, can be readily achieved by this invention in a manner superior to those of any existing devices used for a similar function.

DETAILED DESCRIPTION

A linear activated medicament infusor unit 10, of the type contemplated by the present invention, includes a tubular container 12 open at one end, a resilient plug or piston 14, and a substantially rigid hollow tubular infusor means 16 carried by a frame having a sharpened cannula 18 suitably supported and in communication with one end of the tubular infusor means 16.

Referring now to FIGS. 1 through 5, the infusor 16 includes a framework having a base 20 and a pair of sidewalls 22 symetrically placed on either side of the axis of the frame. In this instance, the sidewalls 22 are reinforced by ribbing 24 which can be eliminated in smaller model designs. The upper or opposite end of the sidewalls 22 are joined by a yoke 26 having a central aperture 28 for acceptance of the vial 12 and a pair of laterally extending flanges or wings 30 for grasping by the index and middle finger of the operator. In this embodiment the reinforcing ribs 24 are curved at their upper extremity for accommodation of the operator's fingers.

In the present embodiment, the cannula 18 is insert-molded centrally of the base 20 and gripped at spaced points 32 and 34, the latter being accomplished by use of spaced walls 36 which re-enter and join at point 34. This technique permits the grasping of the cannula 18 to more positively locate it during the injection molding of the infusor. The bridge formed by walls 36 and re-entrant portion 34 carry a transparent tubular member 38 having a hollow interior bore 39 larger in diameter than the cannula 18 and in communication therewith. This forms a transparent chamber which will be discussed hereinafter. At the upper end of tubular member 38 is a probe or spike 40 which can be best seen in FIG. 5. The probe 40 in this embodiment includes a frustoconical portion 42 having a pre-determined major and minor diameter which is spaced a short distance from the end of the tubular member 38. The end is tapered to provide a sharp point 44 with a large opening to the interior bore 39 of tubular member 38. Intermediate the tip 44 and the frustoconical portion 42 is an annular enlargement 46 for purposes best set forth hereinafter. Spaced axially from the cone 42 is a tapered annular flange 48 whose function will be described hereinafter. It should be noted that the distance between the major diameter or frustoconical portion 42 and the flange 48 is controlled. Thus, the major diameter of the frustoconical portion 42 forms a shoulder 50 in opposition to the flange 48, for purposes best set forth hereinafter.

The vial 12 is a tubular member which is shown to be cylindrical in this embodiment but could be square, elliptical, or any other suitable cross sectional configuration. The vial is open at one end 60 and includes a necked in portion formed by a rib 62 having a pre-determined axial extent and an external groove 64. In this embodiment the rib 62 has a wall thickness substantially equal to the balance of the vial but could be replaced by other suitable spaced protuberance means to form the necked in portion.

The plug or piston 14 is a resilient elastomeric member including a body 70 having a plurality of rings equal to or slightly larger than the internal measurement of the vial 12 and complementary to its cross-sectional shape, in this instance, cylindrical. The rings are axially spaced and in the present embodiment there is a first ring 72 adjacent the outer end of the piston 14; a second ring 74 intermediate the extremities of the piston and spaced from the first ring 72 a distance substantially equal to the axial extent of rib 62; and a third ring 76 at the inner or opposite end. The inner end face 78 is generally concave and leads in its center portion to the bore 80. The bore 80 is sealed by a transverse diaphragm 82 and has a tapered entryway 84 at the outer end and an inwardly directed annular rib 86 which restricts the bore 80 and provides a pair of oppositely directed shoulders 88 and 90. The inside shoulder 88 and the diaphragm 82 serve to form a chamber 92 which is generally frustoconical in cross section and equal to or slightly larger in volume than the frustoconical portion 42 of the probe, for purposes best set forth hereinafter. Further, it will be noted that the rib 86 has an internal transverse measurement equal to or less than the minor diameter of the frustoconical portion 42.

Figures 1, 2, 3, 4, 5:
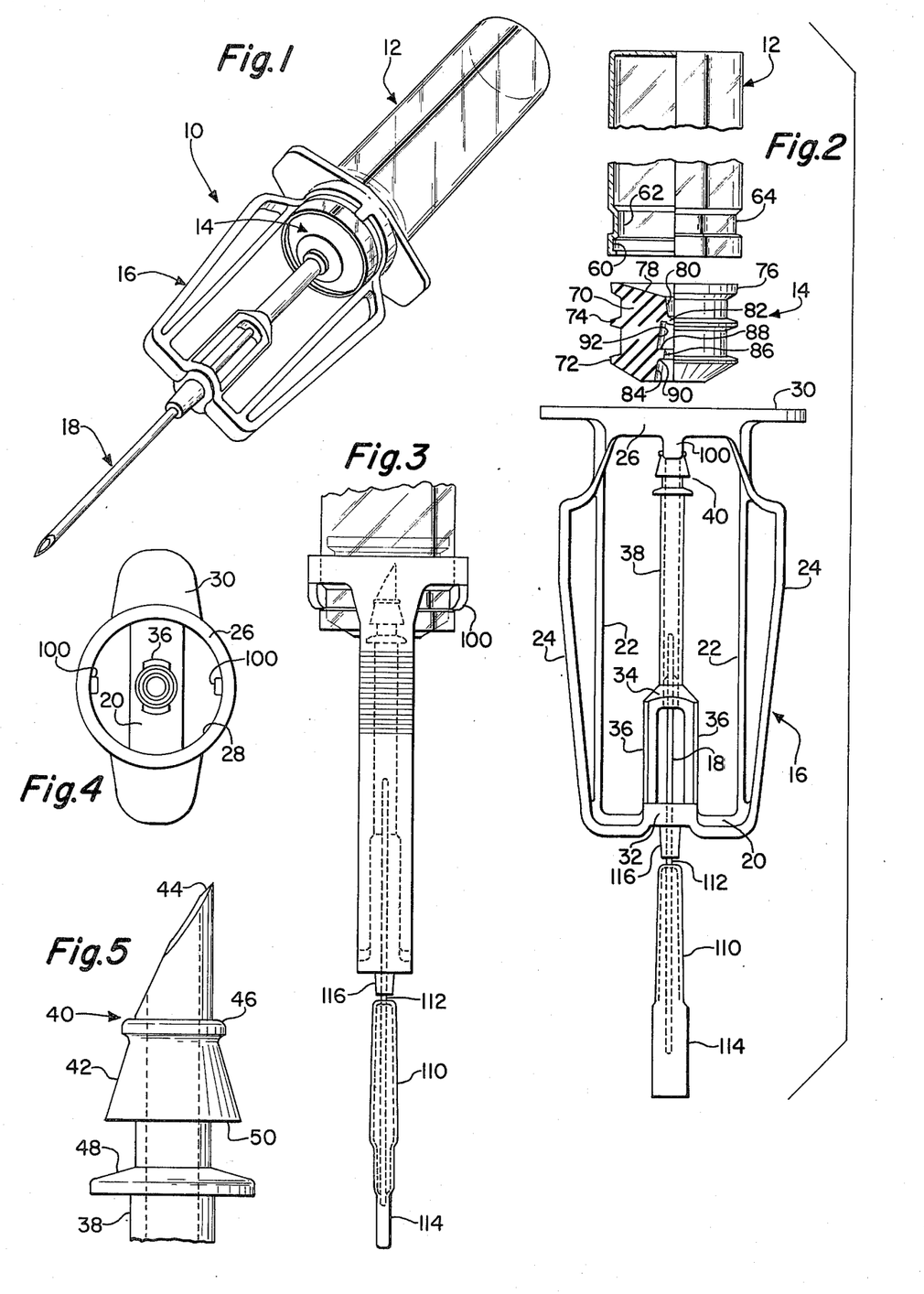
FIG. 1 is a perspective view of a preferred embodiment of the present invention in its assembled relationship.
FIG. 2 is an exploded view of the various elements of the preferred embodiment.
FIG. 3 is a side elevational view in partial section of the device shown in FIG. 2 in assembled relationship.
FIG. 4 is an end view of the infusor unit shown in FIGS. 1 through 3.
FIG. 5 is an expanded elevational view in partial section of the probe of the infusor unit.
Figures 6, 7, 8, 9, 10, 11:
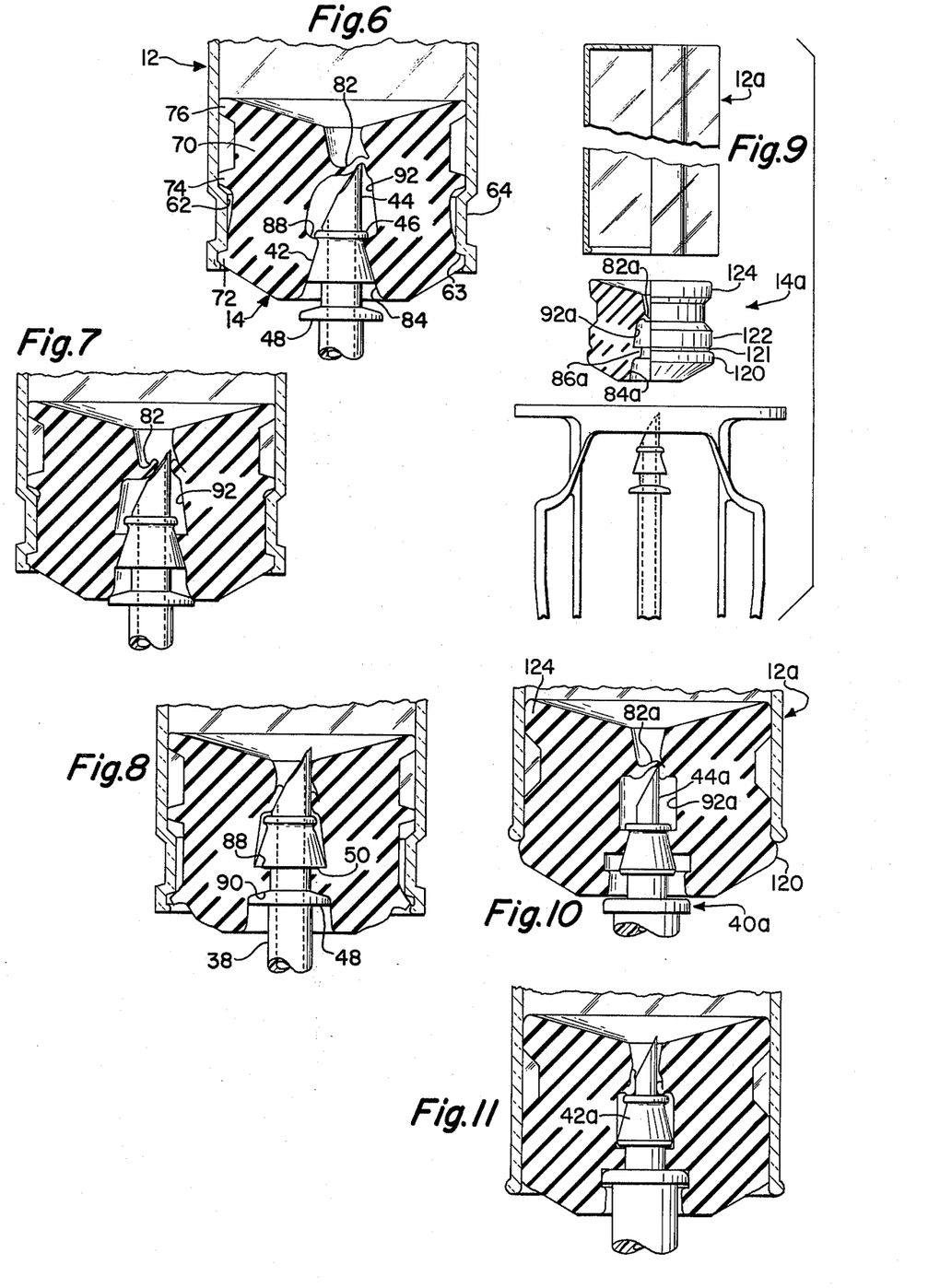
FIG. 6 is an elevational view in partial section of the probe, piston and vial in pre-assembled relation.
FIG. 7 is an elevational view in partial section showing the probe as it makes its initial penetration of the diaphragm in the piston bore.
FIG. 8 is an elevational view in partial section showing the probe in its final seated position at the beginning of the evacuation of material from the vial.
FIG. 9 is an exploded view of the elements making up a second embodiment of the infusor unit.
FIG. 10 is an elevational view in partial section showing the pre-assembly of the probe with the piston of said second embodiment.
FIG. 11 is an elevational view in partial section showing the probe of the second embodiment in final seated position.

Referring now to FIGS. 6 through 8, the piston 14 is assembled with the vial 12 with the first and second ring 72 and 74 disposed on opposite sides of the rib 62. The probe 40 is introduced into the tapered entryway 84 and through the aperture formed by rib 86 resulting in a lateral compression of the resilient rib 86 until such time as the annular rib or ring 46 enters the chamber 92 and rests on the shoulder 88. The axial disposition of the various parts on the probe, including point 44, is such that the bevelled point 44 will distort the diaphragm 82 and the frustoconical portion 42 will cause the piston 14 to bulge sideways into intimate engagement by increase of the surface area of rib 72 and the intermediate portion of the body 70 in contact with the rib 62 and its outwardly-facing shoulder 63. In this fashion the probe can be pre-assembled with the closed vial for storage prior to usage, as will be set forth hereinafter. To assist in maintaining the telescopic relationship between the probe, vial, piston and the general framework, the ring-like yoke 26 is provided with a pair of depending resilient members or fingers 100, as best seen in FIGS. 2 and 3. These fingers 100 will engage in the grooves 64 and prevent inadvertent disassembly from this pre-assembled position.

Further axial thrust of the probe 40 into the bore 80 of the piston 14 causes greater outward forces to be applied to the elastomeric piston so that it distorts and frictionally engages the sidewall of the vial 12, and more particularly, insures engagement between the annular rib 62 and the body 70 of the piston. This relative axial movement between the piston and the probe results in a rupturing of the diaphragm 82 with the frustoconical portion 42 moving axially, as seen in FIG. 7, until its larger lower end, and particularly its shoulder 50, clears the internal shoulder 88 against which it seats. The flange 48 is then positioned against the outer shoulder 90 and due to the volume of the chamber 92, a major amount of the lateral forces incurred in the telescoping operation are removed and the piston 14 reverts to substantially its initial shape. The locking action incurred by the introduction of the probe 40 is primarily due to the side pressure against the vial by the frustoconical configuration of part 42 and its associated flange 48 which keeps the piston stationary with respect to the vial while the probe is being advanced through the piston. It is this combination of drag, or holding power, between the piston and vial, as well as a partial hydraulic lock, which holds the piston while the diaphragm is being punctured. It is preferable to employ this mechanical lock or drag rather than relying totally on hydraulic locking since the latter increases pressure to the drug causing squirting when the tip pierces the diaphragm. Thus, a combined balanced use of these forces will provide the best detent and differential action for initial engagement of the probe and subsequent puncture of the piston by a simple, straightforward linear motion. It will be appreciated that when the probe 40 is in the pre-assembled position, as seen in FIGS. 1, 3 and 6, all of the contact surfaces of the vial and the bore 80 of the piston are closed or covered in such a fashion that it is possible to maintain aseptic conditions at that end of the infusor prior to injection of the medicament. Additional axial force on the vial 12, after puncture as seen in FIG. 8, results in an evacuation of the contents in vial 12 through the interior of the probe 30, the hollow transparent tubular portion 38, and thence through the cannula 18 into the patient, either by venipuncture or through intramuscular injection.

As best seen in FIGS. 2 and 3, the cannula is protected by a cover 110 which can, if desired, be integrally molded to the needle and provided with a fracture point 112 at its juncture to the frame and, at the opposite end, as illustrated, can be closed by crimping, by suitable means such as heat or ultrasonics, to provide a flat portion 114 to seal off the free or sharpened end of the cannula for the function of maintaining aseptic conditions as well as protecting the sharpness of the ground end.

In the use of this embodiment of the invention the entire assembly can be shipped with the vial pre-assembled to the probe or, alternatively, can be packaged separately. In either event, the nurse or doctor can preassemble, if it has not already been so done, by inserting the vial into the cylindrical yoke 26 and by a simple axial pressure, seat the probe in the position shown in FIG. 6. Further axial force on the closed end of the vial 12 will puncture the diaphragm 82, as seen in FIG. 7, until the probe is seated in the chamber 92. With the plug being distorted laterally until the probe is seated, the present design permits the point to continue penetration well beyond the minimum puncture to insure establishment of clear fluid flow. The chamber 92 also gives rise to a sudden drop in penetration force, creating a good detent feel for tactile feedback that the puncture has been made. If it is found necessary to use the drug, the operator will grasp the flattened portion 114 of the needle cover 110, fracture the juncture 112 by twisting, and axially remove the cover 110 to provide a sterilized cannula that is only momentarily exposed to aerobic conditions. Additionally, by carrying out the puncture of the diaphragm before breakage of the needle seal it is possible to eliminate any possibility of hydraulic discharge caused by pressures developed during penetration of the spike into the piston. Thus, for the nurses setting up medicaments, particularly for use in the operating room, this product, with its minimum number of parts, is capable of being activated for use with only one motion, namely, jamming the vial into the probe penetrating point. No "coupling up" is necessary nor are there any magical rotational forces required to insure proper usage. In the event a venipuncture is performed, after air has been cleared from the tubular portion 38 and the cannula 18, aspiration, by slow withdrawal of the vial 12 will reveal that a good venipuncture has been made since the blood can be seen in the transparent tubular portion 38 without introduction of such blood into the vial 12. This is particularly important where the medicament in the vial 12 may be viscous in nature.

It will be recognized by those skilled in the art that the clear tubular portion 38 could be extended to the base 20 and its central portion 32 and communication provided through a Leur fitting 166 and the inserted molded cannula 18 not provided. An independent cannula having a female Leur fitting (not shown) could then be utilized should this be found desirable. The function of the device would remain substantially identical.

In the first embodiment the plug 14 was provided with three substantially identical annular ring members 72–76 which cooperated with the rib 62 for maintenance of the plug 14 relative to the vial 12 during introduction of the probe 40. Referring now to FIGS. 9 through 11, it can be seen that a similar plug 14a can be used with a vial 12a having a generally smooth interior wall that does not have an internal rib, as was found in the first embodiment. The disposition of the entry 84a, the rib 86a, the chamber 92a, and the diaphragm 82a, are substantially identical to the first embodiment. The major difference in this embodiment is the disposition and axial extent of the annular rings 120, 122 and 124. The ring 122 is positioned immediately adjacent to the first ring 120 and is separated therefrom by a minimal groove 121. When the piston 14a is introduced into vial 12a, a ring 120, having a slightly larger diameter than ring 122, is positioned atop the outermost open end of vial 12a, as best seen in FIG. 10. The introduction of the probe 40a causes a lateral swelling until the ring 120 sits in overlying relationship. Until such time as the frustoconical portion 42a is positioned within the chamber 92a, the piston, due to its excessive drag and the overriding ring 120 is substantially locked relative to the sidewall of the vial 12a, thereby permitting puncture of the diaphragm 82a by the tip 44a. Operation of this device is substantially identical to the first embodiment.

Figure 12:
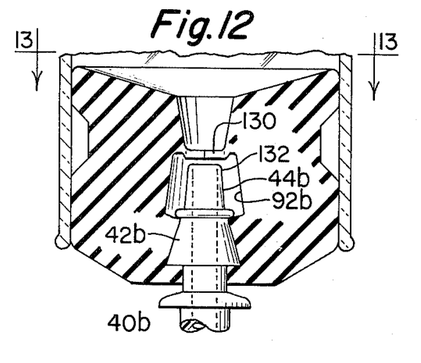
FIG. 12 is an elevational view in partial section of a third embodiment of the present invention.
Figure 13:
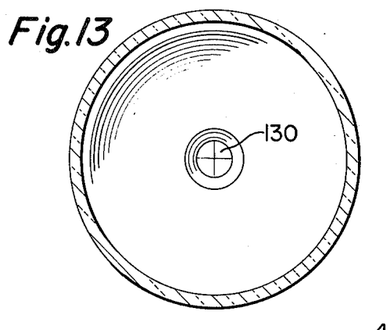
FIG. 13 is an end view of the third embodiment as taken along Line 13—13 of FIG. 12.

Each of the two previous embodiments have been described as having imperforate diaphragms 82 and 82a. Under certain circumstances, it can be desirable to have a diaphragm 130, as seen in FIGS. 12 and 13, which is pre-slit. Thus, the point 44b in this embodiment is not cut on the bias but rather is slightly tapered and provided with a blunt nose 132 for opening the slit diaphragm when the probe 40b is moved axially relative to the piston 14b to seat the frustoconical portion 42b within the chamber 92b. The operation for preassembly, injection, etc., is substantially identical to the previous two embodiments.

Figure 15:
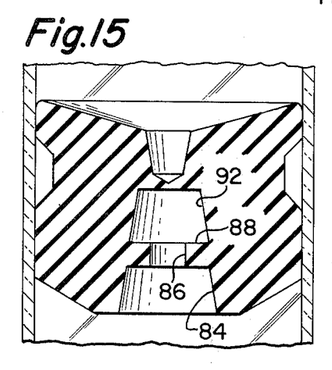
FIGS. 15 and 16 are variations on the interior bore chamber of the piston used with the present invention.
Figure 16:
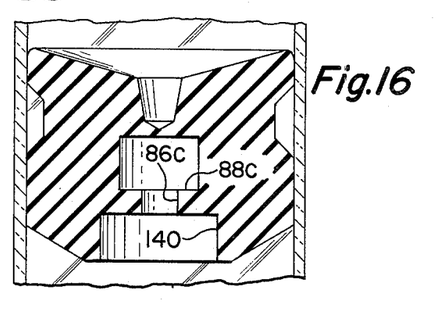

While the factor of aspiration by movement of the vial has been previously discussed in a general manner, it should be recognized that aspiration is possible, but also can be controlled. It has been found that where the sidewalls of the entryway 84 substantially support the rib 86 there is a very short moment arm and hence the rib is rigidified and aspiration is possible. For example, if the entryway 84, as seen in FIG. 15 and the previous embodiments, is frustoconical in section with the narrower portion adjacent the rib 86, there is little tendency for the rib to move downwardly, as viewed in the drawing. If, however, the entryway is counterbored, as shown at 140 in FIG. 16, it can be seen that there is a greater degree of space for the rib to move into, either by flexing or crushing, when a retrograde movement is applied to the probe. Such a configuration would prevent aspiration to a substantial degree since the probe would readily disengage, with its shoulder 50, not shown, coming disengaged from shoulder 88c by flexure of the rib 86c downwardly into the counterbore 140. This would be an ideal configuration for those instances where aspiration would have a negative value and where quick removal of the vial for replacement by a second vial would be desired. It has been found that when the configuration shown in FIG. 15 and the previous embodiments have been used, the shallow undercut beneath the corner of rib 86 will not release the prove during aspiration unless a high force rapidly applied will cause this rib 86 to bend downwardly and compress outwardly, as by beam loading, to bend the short arm out of the way. Thus, aspiration is possible when the vial is withdrawn slowly but will result in removal of the piston from the probe if a quick force is applied in a retrograde direction to the vial.

Figure 14:
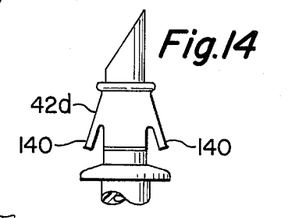
FIG. 14 is an elevational view in partial section of an alternate design for the probe.

On the other hand, it is conceivable that there are instances where it would be desirable to provide aspiration in a positive fashion. To this end, the probe can be varied by undercutting two sides of the frustoconical section 42d as seen in FIG. 14, to provide a pair of resilient arms 140 that will flex during insertion and seat against the shoulder 88 in a positive fashion which will substantially prevent removal from the chamber 92.

Figure 17:
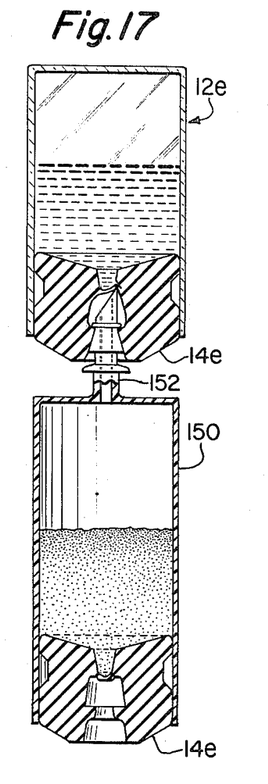
FIG. 17 is an elevational view in partial section of a device using the teachings of this present invention for the purpose of having two vials for storage of liquid and dry materials which cannot be pre-mixed until immediately before injection.
Figure 18:
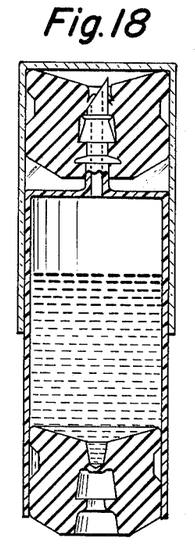
FIG. 18 is an elevational view in partial section of the device shown in FIG. 17 when the materials have been mixed.

For certain types of drugs such as pentothal, which have short post-mixture life, crystals can be packaged for subsequent hydration into administerable form. In FIGS. 17 and 18 the vial 12e is substantially identical to the embodiment shown in FIGS. 9 through 11 with a piston 14e of similar configuration. This vial would be filled with a liquid solution, such as water, and preferably would be a glass vial. A second vial 150 has its lower end in communication with a probe 152 having a configuration substantially identical to the probe used in the embodiments shown in FIGS. 1 through 11. The vial 150 has a diameter equal to or less than the internal diameter of vial 12e and would generally contain and be manufactured from a material compatible with the dry crystals of the drug which must be hydrated. To accomplish hydration, the probe 152 is forced through into pierced relationship with the piston 14e in vial 12e. Axial telescoping of vial 150 into vial 12e results in the introduction of the liquid in vial 12e into vial 150, in a manner shown in FIG. 18. As will be appreciated by those skilled in the art, the two vials would initially be activated in the position shown in FIGS. 17 and 18. When the liquid is transferred from vial 12e to vial 150 there is a tendency for the air in the free space of the two vials to become compressed and tend to force the two vials apart when operator-applied force is removed. Thus, the operator preferably should hold the two vials in the position of FIG. 18; insert the premixed assembly into an infusor; penetrate the diaphragm of piston 14e in vial 150; invert the infusor and carefully bleed off the air while holding the second vial immobile relative to the first vial to thereby prevent expulsion of the drug prior to injection in the patient. To overcome such manipulative action by the operator it would be possible to provide a rotatable or snap action locking collar, not shown, to maintain the vials in the position shown in FIG. 18.

It is also contemplated that the piggy-back preassembly of FIG. 17 could be packaged in an attractive tubular cover, not shown, that would lock the two vials in this position, provide a tamperproof cover and yet permit axial collapse for telescoping the vials for mixing before exposure to atmospheric conditions. The piggyback telescoped vials would then be inserted into an infusor unit and the hydrated medicament could then be injected into the patient in the fashion described hereinbefore.

Figure 19:
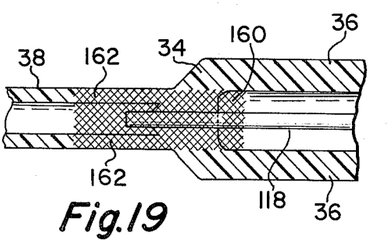
FIG. 19 is a plan view in partial section of a filtration device for use with the present invention.
Figure 20:
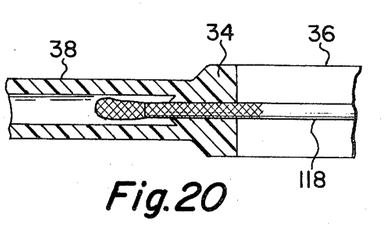
FIG. 20 is a side view in partial section of the device shown in FIG. 19.

In order to insure that foreign matter which might be inadvertently found in a medicament or a crystal from a hydrated medicament, not be introduced into the patient's blood vein, a filter device can be introduced into the construction of the present invention. Referring now to FIGS. 19 and 20, the contemplated filter includes a strip of porous filter material which is bent back upon itself to cover the end of the cannula 118 at the point it leaves the yoke 34 and enters the hollow tubular portion 38. The filter 160 would be bound along its free open edges 162 by the plastic materials forming the tubular portion 38 and the bridge 34, thereby forming an envelope which encloses the free end of cannula 118. This can be accomplished at the time of insert molding the needle into the framework of the infusor unit.

From a manufacturing standpoint, it will be appreciated that the fabrication of the infusor unit with its framework, insert molded cannula and cover, can be accomplished on standard injection molding equipment. The cannula is adequately held intermediate its length so that damage is not done to the ground point. The cover can be simultaneously molded and sealed at a secondary operation. This eliminates subsequent processing, such as glueing or assembly of the needle to the end of a framework, and, assuming that the parts are "clean", sterilization of the drug container and infusor attached together sterilizes all fluid conducting passages and all primary and secondary drug contact surfaces. Depending on the needle cover design and packaging of the entire unit, these surfaces will remain absolutely sterile until the moment of use when the needle is exposed to air seconds before venipuncture. Using the fewest possible parts and attaining the maximum variable end configurations makes this item a broadly based economical product. The only cause for component difference requiring separate tooling is dosage size variation and needle size. However, they add significant substitute possibilities to the overall system.

From an operating room standpoint, the presence of the transparent tubular element 38, forming a chamber larger than the cannula, provides a ready visible observation of an accurate venipuncture and substantially lowers the pressure of the blood, thereby substantially reducing the possibility of the introduction of blood into the drug container. Additionally, more than one drug can be administered sequentially to the same patient without removal of the cannula from the venipuncture and when telescoped vials of the type described herein are utilized, drugs having a short life span following hydration can be pre-assembled to a needle in a rapid manner.

The infusor unit can be fabricated from known transparent thermoplastic materials such as polypropylene. The pistons or plugs are commonly made from an elastomeric material such as rubber while the vials can be fabricated from materials which are compatible with the drugs stored therein. In most instances, glass vials will be utilized with the exception of where piggyback installations require the molding of a probe and aperture at the normal enclosed end of the vial. There, a suitable plastic material compatible with the drug stored therein in its dehydrated condition can be used. For sterile packaging of the device, either in pre-assembled or side-by-side disassembled condition, vacuum formed packaging commonly known as blister-packs will provide the necessary sterility for storage and handling of devices of the type contemplated herein.

While the various embodiments disclose the basic teachings of this invention, it will be appreciated by those skilled in the art that other combinations of materials and structure can be used.

I claim:

1. A medicament infusor unit including a tubular container open at one end, a resilient piston having a central bore blocked by a transverse imperforate diaphragm means adapted to cooperatively seal the end of said container, a substantially rigid hollow tubular infusor means having means to secure a sharpened cannula which extends outwardly therefrom and in communication with one end thereof and the other end of said infusor having means adapted to cooperate with means in said piston to sealingly engage therewith, means on said infusor at said other end for cooperatively penetrating said diaphragm to provide access of the rigid hollow infusor to the interior of the piston sealed tubular container, said piston and said container having controlled configurations, sizes and relative moduli of friction such as to permit axial insertion, diaphragm penetration, and locking of the infusor within the piston solely by an axial movement without relative axial motion between said piston and container, but permitting such relative movement between the piston and container after the infusor has penectrated and is seated within said piston, and means on said infusor for manipulation relative to said container, said container including a reduced dimensional portion adjacent its open end to provide a point of interference with said piston which is formed of an elastomeric material, said piston being provided with a plurality of radially extending annular rings about its periphery in spaced axial relation, the central bore of said piston including an interior chamber closed at one end by said diaphragm means and a reduced entryway at its open end, said reduced entryway and said chamber at its open end defining a positive interior shoulder adapted to cooperate with a shoulder means on said infusor, said infusor at its free end includes a sharp tapered point opening to the hollow interior thereof with said sharp point formed by one or more diagonal planes intersecting a cylinder on the bias, said point being axially spaced from first shoulder means for cooperation with the interior shoulder formed by said chamber at its junction with the reduced entryway, having a diametrical extent less than the larger dimension of said first shoulder means but greater than said reduced entryway, the axial extent of said chamber and the resiliency of said diaphragm being controlled relative to the axial extent of said tapered point from its sharpened tip to said protuberance means to permit telescopic preassembly of the infusor with the piston without penetration of said diaphragm by said point, said protuberance means engaging the first shoulder means formed by said chamber to prevent inadvertent removal of said infusor from said piston.

2. A device of the type claimed in claim 1 wherein said piston bore includes a counterbored entry leading to said reduced entryway which communicates with said chamber and forming a second shoulder means positioned adjacent said counterbore outside of and in spaced axial relation to the internal chamber shoulder means, said infusor including laterally extending flange means axially spaced from the larger dimension of said first shoulder means to form a pair of opposed spaced shoulders and adapted therewith to grip that radially inwardly directed ring-like portion of the piston defined between the two said piston shoulder means for lockingly engaging the infusor with said piston after penetration of the diaphragm by the pointed means.

3. A medicament infusor unit including a tubular container open at one end, a resilient piston having a central bore blocked by a transverse diaphragm means adapted to cooperatively seal the end of said container, a substantially rigid hollow tubular infusor means having means to secure a sharpened cannula which extends outwardly therefrom and in communication with one end thereof and the other end of said infusor having means adapted to cooperate with means in said piston to sealingly engage therewith, means on said infusor at said other end for cooperatively penetrating said diaphragm to provide access of the rigid hollow infusor to the interior of the piston sealed tubular container, said piston and said container having controlled configurations, sizes and relative moduli of friction such as to permit axial insertion, diaphragm penetration, and locking of the infusor within the piston solely by an axial movement without relative axial motion between said piston and container, but permitting such relative movement between the piston and container after the infusor is seated within said piston, and means on said infusor for manipulation relative to said container, said infusor unit includes an elongated frame having a base positioned adjacent the means for gripping the sharpened cannula, axially extending substantially rigid members integral with said base and positioned in spaced relation from each other, means connected to at least one of said members at the opposite end, said infusor being positioned generally centrally and spaced from said axially extending members whereby said container, upon movement relative to the piston, is restrained against lateral movement within said connected means at said opposite end.

4. A device of the typed claimed in claim 3 wherein said cannula intermediate its ends is embedded in said base and extends on opposite sides thereof, a yoke-like means integral with said base and extending interiorly of said unit and adapted to grip said cannula adjacent its free end opposite said sharpened end, said rigid hollow infusor having a first portion chamber whose interior is visually perceivable through its side walls, said chamber extending axially and integrally from the end of said yoke opposite said base in communication with said cannula free end and terminating in a second portion defining a laterally extending means larger in dimension than and terminating adjacent the opposite end of the infusor unit for cooperation with said piston and positioned internally of and in laterally spaced relation to the rigid members, whereby aspiration of fluids by the infusor unit can be visibly seen within said first portion chamber without contamination of the contents of said container.

5. A device of the type claimed in claim 4 wherein said connecting means attached to said rigid members includes a generally cylindrical web adapted to accept said container interiorly thereof.

6. A device of the type claimed in claim 5 wherein said manipulating means includes a pair of laterally extending flange means defining gripping means for acceptance of two or more digits of the operator's hand and positioned at said opposite end of the rigid member.

7. A device of the type claimed in claim 6 wherein said piston is in the form of a plunger of an elastomeric material having a plurality of radially extending rings axially spaced thereon which are dimensionally greater than the interior measurement of said container to resiliently, sealingly and grippingly engage the interior wall of said container, said container including an internally directed rib having an axial extent generally equivalent to the spacing between at least one pair of said rings whereby said piston, after filling the container with a medicament, is positioned generally internally of the container with said pair of rings positioned on opposite sides of said rib prior to engagement with said infuser point.

8. A device of the type claimed in claim 1 wherein said container is a substantially cylindrical vial having smooth side walls and closed at one end, said piston having a plurality of laterally extending flexible rings with a pair of said rings being positioned adjacent the exposed end of the piston when it is inserted within the vial with the lip or free end of the vial being axially positioned intermediate said pair of rings, said piston bore having a countersunk aperture in its exposed position communicating with an intermediate chamber with a reduced diameter entry forming interior shoulder means, second shoulder means outside of the chamber being positioned axially between the chamber and said countersunk opening, said infuser point having a frusto-conical portion increasing in diameter from the tip to form a shoulder means, a laterally extending flange axially spaced from said shoulder means and adapted with said shoulder means to cooperate and interlock the infuser point with said piston when said shoulder means of the infuser are positioned in engagement with the shoulder means of the chamber, the introduction of said frusto-conical portion into said reduced entryway to the chamber forcing said elastomeric piston radially outwardly whereby said first ring will override the free end of the vial and prevent movement of the piston during the insertion of the frusto-conical portion into the chamber and introduction of the pointed end through the diaphragm, after interlocking the point with the piston, further axial movement of the vial relative to the infuser results in movement of the piston into the vial and expulsion of material contained in the vial through the infuser and then into communication with the cannula.

9. A device of the type claimed in claim 1 wherein said container includes in its closed end a hollow rigid pointed member extending outwardly from said container with its holllow interior in communication with said container, a second container including a piston similar to the first container with said second container having an interior dimension at least equal to the outer dimension of said first container, said first container, said first container carrying a dry substance while said second container carries a liquid, relative movement between said containers and movement of the point on the end of the first container through the diaphragm of the piston in the second container providing access for the liquid in the second container to be transmitted into the first container to admix and place the dry material in solution, the telescoped double container then being capable of infusion by axial introduction with the infusor.

10. A device of the type claimed in claim 3 wherein said central bore of said piston includes an interior chamber closed at one end by said diaphragm means and a reduced entryway at its open end, said means for penetrating said diaphragm includes a pointed end which is provided with a plurality of radially and axially outwardly extending resilient wing members adapted to be compressed during axial insertion within said entryway and expanded within said chamber for positive retention with a shoulder formed in the said chamber in the piston to insure aspiration of the piston relative to the container.

11. A device of the type claimed in claim 4 wherein said container includes a groove on the container outer wall, stop means carried by the infusor and engageable with the said groove and adapted to permit telescopic movement of said container in one direction relative to said infusor unit but preventing unintentional retrograde movement in the opposite direction.

12. An infuser unit of the type claimed in claim 2 wherein the flexibility of said ring-like portion is controlled by dimensionally controlling the radial and axial extent of said portion in relation to the volume of said countersunk entry and the shape and size of the infuser point whereby the application of a slow limited retrograde axial movement applied by the infuser tapered point results in movement of the piston in a retrograde direction relative to the container and aspiration by the container while rapid application of an axial force will pop the tapered infuser point out of locked engagement with said piston by outward deformation of said ring-like portion from its captured position between the shoulders on said infuser and thereby permit association of a second sealed container with said infuser while maintaining implant of the cannula in a patient.

13. An infuser unit of the type claimed in claim 3 wherein said tapered point includes a plurality of flexible means adapted to permit ready introduction of said point into said piston but precluding removal thereof to insure single dose usage of said infuser.

14. An infuser unit of the type claimed in claim 12 wherein said laterally extending flange means on said infuser insures infusion by movement of the piston into said container with at least one of said frustoconical portion and said ring-like portion of the piston being so dimensioned as to permit said frustoconical portion to readily override said ringlike portion and thereby preclude retrograde movement of the piston relative to the container with its aspirating effect on the cannula.

15. An infusor unit of the type claimed in claim 4 wherein said sharpened cannula is encased in an axially extending protector initially open at its free end but capable of being sealed around said sharpened point without damage to said point and axially removable therefrom.

16. An infusor unit of the type claimed in claim 15 wherein said protector is generally cylindrical through a substantial portion of its extent and frangibly connected to the means for securing the cannula, the free end of said protector being sealed by heat deforming means into a closed non-circular configuration which is adapted to serve as a manipulative means for gripping during fracture of the frangible means.

17. An infusor unit having an infusor communicating with a cannula for the parenteral administration of a medicament contained in a tubular vial having at least one open end, said open end sealed by a resilient piston which includes an axial bore interrupted by a transverse diaphragm sealing member, said infusor including a base, a substantially axially rigid open frame connected to said base and adapted to telescopically accept said vial within said frame from the end opposite said base, means for securing a cannula on said base in outwardly extended position opposite to said frame, hollow rigid probe means communicating with said cannula and extending axially within said frame and adapted to sealingly engage said piston bore when telescoped therewith, said probe including a free end having means adapted to urge said piston laterally into firm engagement with the wall of said vial by temporarily increasing the area of contact by said piston with said vial and thereby temporarily increasing the friction to a point necessary to maintain the piston in substantially fixed position with said vial while second means on said free end is adapted to traverse said diaphragm and provide communication with the interior of said vial, whereby when said probe means has traversed said diaphragm and it is positioned in sealed relation to said piston the lateral forces are removed with the piston impositively fixed relative to said probe and readily capable of movement relative to said vial for expulsion of the contents through said communicating probe and cannula when said vial is axially telescoped into said frame whereby the contents of said vial can be quickly administered with an axial movement of said vial, said probe including at its free end a hollow sharp tip, shouldered means spaced from and directed away from said tip, and a laterally extending flange spaced from said shouldered means, said probe further including a hollow rigid translucent intermediate portion communicating at opposite ends with said sharp tip and said cannula, said shouldered means and said flange serving as a pair of spaced opposed shoulder means.

18. An infusor of the type claimed in claim 17 wherein said cannula is fixedly secured relative to said base.

19. An infusor of the type claimed in claim 17 wherein said cannula is provided with a fitment for removably mating with a complementary sealing fitment on said infusor.

20. An infuser of the type claimed in claim 17 wherein said piston is formed of an elastomeric material having an axially extending bore traversed by a sealing diaphragm, an open chamber formed in said bore and defined by said diaphragm at one end and an annular resilient ring-like flange projecting substantially radially into said bore to form a reduced entryway into said chamber, opposite axially spaced sides of said flange forming shoulder means adjacent said entryway, said bore being chamfered to serve as a centering means lead-in to said ring-like flange, annular protuberance means on said probe in the form of a rib-like member having a diametral extent in excess of said reduced entryway, the axial distance from said rib to said sharp tip of the probe being slightly greater than the axial dimension of said chamber whereby when said probe is telescoped into said chamber with said rib engaging the inner chamber shoulder means and the sharp tip axially distorting the diaphragm the probe can be maintained in preassembled sealed relation with the reduced entryway gripping the shouldered means in sealed relationship, said piston further including means on its exterior for sealing engagement with the wall of said vial.

21. An infuser of the type claimed in claim 20 wherein said shouldered means is a frusto-conical portion which has an axial extent equal to or less than said chamber, the axial spacing between the base of said frusto-conical portion and said annular flange being equal to or larger than said ringlike flange, the diametral extent of said frusto-conical portion being controlled relative to the dimensioning of said reduced entryway whereby axial telescoping of the probe beyond preassembled relation is adapted to cause a lateral distortion of said piston against the wall of the vial to create a frictional resistance against said wall in excess of the force required for said sharp tip to traverse said diaphragm and maintain said piston in substantially fixed axial relation to said vial until said hollow sharp tip pierces said diaphragm and thereby gains access and communication with the interior of said vial, when said frusto-conical portion axially passes the reduced entryway and is seated within the chamber and piston returning substantially to its initial configuration and capable of being axially moved within said vial for evacuation of its contents through said probe and cannula.

22. An infusor of the type claimed in claim 17 wherein said intermediate portion of said probe terminates in spaced relation to said base, said cannula being fixed to said base intermediate its extremities with the end opposite its sharpened end communicating with said intermediate portion and means supporting the communicating ends of said intermediate portion and said cannula in fixed relation.

23. An infusor of the type claimed in claim 17 wherein said frame at its end opposite said base includes a transverse portion having an axial opening complimentary to the shape of the vial and co-axial with said probe.

24. An infusor of the type claimed in claim 23 wherein said frame includes finger gripping means for control of said frame during axial manipulation of said vial.

25. An infusor of the type claimed in claim 20 wherein said piston includes a plurality of resilient annular rings, for sealing engagement with said vial wall.

26. An infusor of the type claimed in claim 25 wherein said rings are of limited axial extent and axially spaced from each other, said vial including an internal annular rib adjacent its opening having an axial extent acceptable between at least one adjacent pair of said ribs to assist in increasing the resistance against axial movement of said piston relative to said vial during penetration of the diaphragm by said probe.

27. An infusor of the type claimed in claim 25 wherein said sealing rings are at least three in number with a ring at the first end entering the vial and a second ring at the trailing end slightly larger in diameter than said first ring and initially positioned adjacent to but not completely within said vial, said third ring being axially positioned intermediate the other rings but axially closer to said second ring than said first ring, said first and third rings being initially positioned within said vial, initial introduction of said probe into said piston results in a lateral expansion of said second ring into overlying engagement with the free end lip of said vial and compression of said third ring against the side wall of said vial thereby creating a drag force between said piston and vial in excess of the force necessary for the probe tip to traverse the diaphragm and communicate with the interior of the vial, axial positioning of said frusto-conical portion within said chamber permitting said rings to radially contract thereby releasing said draag resistant force sufficiently to permit said piston with its second ring to be axially moved within the vial for evacuation of its contents through the probe and cannula.

28. An infusor of the type claimed in claim 20 wherein said diaphragm is imperforate and must be pierced by said probe.

29. An infusor of the type claimed in claim 20 wherein said diaphragm is slit but self-sealing until contacted by said probe.

30. An infusor of the type claimed in claim 17 wherein the leading end of said piston is inserted into said vial and the trailing end protrudes from said vial and includes a roll-over lip which extends laterally from said trailing end and thence axially in parallel radially spaced relation to the side wall of said piston to grasp the free end and a portion of the external wall of said vial when the piston is mounted therein whereby said piston can be maintained in said position relative to said vial when subjected to a substantial vacuum within said vial.

31. In an infusor of the general type described, a filter device including a strip of filter material permeable to body fluids bent back upon itself to form a sleeve having a bight portion and opposite edges; a cannula with one end positioned within said sleeve and means forming a chamber communicating with said bight portion grippingly engaging the edges of said strip and fixing said cannula relative to said filter.

32. In an infusor of the type claimed in claim 31 said filter edges and said cannula being insert molded in thermo-plastic material forming said chamber.

33. An infusor of the type claimed in claim 21 wherein said counterbore terminating at said ring-like flange is frusto-conical in section and provides only a shallow undercut of small radial extent to the exposed portion of said ring-like flange whereby said flange is axially supported and relatively non-flexible in the direction of retrograde movement of the probe relative to the piston.

34. An infusor of the type claimed in claim 21 wherein said counterbore eentry to said reduced entryway in said ring-like flange is generally cylindrical in section and provides a relatively large undercut or radial extent to the exposed portion of said ring-like flange, said flange being readily flexible in the direction of retrograde movement of the probe relative to the piston whereby said piston when associated with said probe is movable more readily in the direction of evacuation of the vial than in the direction of aspiration of the cannula.

35. An infusor of the type claimed in claim 17 wherein said vial at the end opposite the open end includes an axially outwardly extending hollow probe communicating with the interior of the vial and adapted to sealingly cooperate with a piston contained in a second vial, said second vial having an internal configuration greater in size than the external complimentary configuration of said first mentioned vial, whereby differing materials in the two vials can be mixed and the mixture dispensed from said first vial and administered through said infusor.

36. A piston-like plug for use with an open ended vial including an axially extending bore traversed by a sealing diaphragm, an open frusto-conical chamber formed in said bore and defined by said diaphragm at the small end thereof and an annular resilient ring-like flange projecting substantially radially into said bore to form a reduced entryway into the large end of said chamber, said entryway being axially spaced from the open end of said bore opposite axially spaced sides of said flange forming shoulder means adjacent said entryway, a plurality of resilient annular rings axially spaced along the exterior of said piston for sealing engagement with said vial wall.

37. A piston of the type claimed in claim 36 wherein said rings are of limited axial extent and axially spaced from each other, said vial including an internal annular rib adjacent its opening having an axial extent acceptable between at least one adjacent bore of said ribs to assist in increasing the resistance against axial movement of said piston relative to said vial during penetration of the diaphragm by a suitable probe.

38. A piston of the type claimed in claim 36 wherein said sealing rings are at least three in number with a ring at the first end entering the vial and a second ring at the trailing end slightly larger in diameter than said first ring and initially positioned adjacent to, but not completely within, said vial, said third ring being axially positioned intermediate the other rings but axially closer to said second ring than said first ring, said first and third rings being initially positioned within said vial.

39. A piston of the type claimed in claim 36 wherein said diaphragm is imperforate and must be pierced by a suitable probe to gain access to said vial.

40. A piston of the type claimed in claim 36 wherein said diaphragm is slit but self-sealing until contacted by a suitable probe.

41. A piston of the type claimed in claim 36 wherein said diaphragm is positioned intermediate the ends of said bore.

42. A piston of the type claimed in claim 38 wherein said second and third rings are positioned in close proximity whereby upon introduction into said vial the void between said second and third rings is filled by the compression of said third ring material and thereby said second and third rings effectively act as a single ring having substantial axial extent and provide substantial frictional resistance to movement along the wall of said vial.

43. A medicament container for use with a substantially rigid hollow tubular infusor means terminating in a frusto-conical portion carrying a work penetrating means at its free end, said container including a tubular vial open at one end, a resilient piston having a central bore blocked by a transverse diaphragm means adapted to cooperatively seal the end of said container, said piston including a frusto-conical interior chamber complimentary to said frusto-conical portion and closed at one end by said diaphragm menas and a reduced entryway at its open end spaced from the open end of said bore, said infusor adapted to be retained and sealed by integral suitable means in said reduced entryway of the piston without having the work penetrating means puncture the diaphragm, said infusor and piston thereby being preassembled to provide sterility behind the puncture zone for maintaining sterility of the piston at the time of puncture of the diaphragm by the work penetrating means.

44. A wet-dry preassembly unit adapted for use with a complimentary hollow rigid pointed infusor communicating with a sharpened cannula, said preassembly including two tubular containers open at one end, two resilient pistons each having a central bore blocked by a transverse diaphragm means with one of such pistons adapted to cooperatively seal the respective open end of each of said containers, one of said containers carrying on its closed end a hollow rigid pointed member extending outward from said container with its hollow interior in communication with the interior of said container, said second container having an interior dimension at least equal to the outer dimension of said first container to permit telescopic association of the first container into the second container, said first container adapted to carry a dry substance while said second container carries a liquid, relative movement between said containers and movement of the pointed member on the end of the first container through the diaphragm of the piston in the secnd container providing access for the liquid in the second container to be transmitted into the first container to admix and place the dry material in solution, the piston disphragm in the first container providing access to the admixed solution by penetration by the complimentary infusor.

45. An infusor unit having means for communicating with an aspirating sealed container, an outwardly extending cannula having a first sharpened end for injection or venipuncture and a second end, an intermediate translucent hollow means connecting said communicating means and the second end of said cannula whereby aspiration of body fluids through said sharpened end can be visually observed in said intermediate hollow means before contaminating said sealed container, and a filter device disposed intermediate said communicating means and the second end of said cannula.

46. An infusor unit having means for communicating with an aspirating sealed container, an outwardly extending cannula having a first sharpened end for injection or venipuncture and a second end, an intermediate translucent hollow means connecting said communicating means and the second end of said cannula whereby aspiration of body fluids through said sharpened end can be visually observed in said intermediate hollow means before contaminating said sealed container, said communicating means includes a hollow generally cylindrical member having a chamfered tip, said sealed container including a vial with one open end and a resilient plunger having a restricted bore communicating with an enlarged internal chamber which is terminated at its other end by a diaphragm, said hollow member including at least one resilient laterally extending spring arm, the free end of which engages said chamber wall to prevent retrograde withdrawal of said member from said restricted bore.

* * * * *